(12) United States Patent
Nakamura et al.

(10) Patent No.: US 8,712,190 B2
(45) Date of Patent: Apr. 29, 2014

(54) COLLATING DEVICE, COLLATING METHOD, AND PROGRAM

(75) Inventors: Yoichi Nakamura, Tokyo (JP); Toshio Kamei, Tokyo (JP)

(73) Assignee: NEC Corporation, Tokyo (JP)

( * ) Notice: Subject to any disclaimer, the term of this patent is extended or adjusted under 35 U.S.C. 154(b) by 215 days.

(21) Appl. No.: 13/123,473

(22) PCT Filed: Oct. 9, 2009

(86) PCT No.: PCT/JP2009/067606
§ 371 (c)(1),
(2), (4) Date: Apr. 8, 2011

(87) PCT Pub. No.: WO2010/041731
PCT Pub. Date: Apr. 15, 2010

(65) Prior Publication Data
US 2011/0194776 A1    Aug. 11, 2011

(30) Foreign Application Priority Data
Oct. 10, 2008   (JP) .................................. 2008-263483

(51) Int. Cl.
*G06K 9/32*   (2006.01)
(52) U.S. Cl.
USPC ............................. 382/295; 382/115; 382/124
(58) Field of Classification Search
None
See application file for complete search history.

(56) References Cited

U.S. PATENT DOCUMENTS

| 4,992,663 | A |   | 2/1991 | Takeo |   |
|---|---|---|---|---|---|
| 5,781,660 | A | * | 7/1998 | Nitta et al. | 382/177 |
| 6,223,181 | B1 | * | 4/2001 | Goldberg et al. | 1/1 |
| 2002/0028004 | A1 |   | 3/2002 | Miura et al. |   |
| 2004/0042645 | A1 | * | 3/2004 | Wang | 382/125 |
| 2005/0105779 | A1 |   | 5/2005 | Kamei |   |
| 2005/0201595 | A1 | * | 9/2005 | Kamei | 382/118 |
| 2006/0002596 | A1 | * | 1/2006 | Takahashi | 382/124 |
| 2008/0123905 | A1 |   | 5/2008 | Ito et al. |   |
| 2008/0240521 | A1 | * | 10/2008 | Miyazaki | 382/124 |

FOREIGN PATENT DOCUMENTS

| JP | 02-001080 A | 1/1990 |
|---|---|---|
| JP | 04-184584 A | 7/1992 |
| JP | 2002-083298 A | 3/2002 |
| JP | 2002-092616 A | 3/2002 |
| JP | 2003-296735 A | 10/2003 |
| JP | 2005-056282 A | 3/2005 |
| JP | 2007-000219 A | 1/2007 |
| JP | 2007-213199 A | 8/2007 |
| JP | 2008-003989 A | 1/2008 |

* cited by examiner

*Primary Examiner* — Jason M Repko
*Assistant Examiner* — David Perlman
(74) *Attorney, Agent, or Firm* — Sughrue Mion, PLLC

(57) ABSTRACT

Provided are a collating device, a processing method and a collation program, in which a reference line is extracted from an image and each partial image is moved in a manner that the reference line becomes a predetermined one thereby to correct the image, and in which the corrected image is collated so that an authentication result can be obtained for a short time period without any rotating operation. At first, a reference line extracting unit extracts the center line or the contour line of the image as the reference line. Next, an image correcting unit moves each partial image in parallel thereby to correct the image so that the reference line obtained by the reference line extracting unit becomes a predetermined one. Moreover, an image collating unit collates the image corrected by the image correcting unit and a predetermined image to acquire an authentication result.

31 Claims, 9 Drawing Sheets

COLLATING DEVICE, COLLATING METHOD, AND PROGRAM

CROSS REFERENCE TO RELATED APPLICATIONS

This application is a National Stage of International Application No. PCT/JP2009/067606 filed Oct. 9, 2009, which claims priority from Japanese Patent Application No. 2008-263483 filed Oct. 10, 2008, the contents of all of which are incorporated herein by reference in their entirety.

TECHNICAL FIELD

The present invention relates to a collating technology.

BACKGROUND ART

The personal identification system is described in Patent Literature 1. This personal identification system includes a light source, an imaging unit, and an image processing unit. A plurality of light-emitting elements, which make the foregoing light source, are arranged according to a shape of a finger. The foregoing light-emitting element is a near-infrared high-intensity LED or a laser beam.

The above-mentioned personal identification system operates as follows.

The foregoing light source outputs a weak light for detecting the finger at any time. The foregoing imaging unit detects whether or not the finger is exposed to the weak light. When it is detected that the finger has been exposed to the weak light, the foregoing light source decides which element of the light source is turned on based upon this finger location information. The foregoing light source acquires pixel value information of the image that is being monitored by the foregoing imaging unit, and optimizes the amount of light to be supplied from the light source. The foregoing imaging unit, after this optimization of the amount of light to be supplied, captures an image of an imaging object (living body). The foregoing image processing unit performs the following image correction (contour extraction/image rotation processing) for the image captured by the foregoing imaging unit. That is, the foregoing image processing unit firstly performs an edge emphasizing processing for the captured image, and extracts the contour position of the finger. The foregoing image processing unit performs the rotation processing based upon this extracted contour so that the finger inclination becomes constant. FIG. 18 shows an example of the contour extraction/rotation processing. FIG. 18(a) is a view illustrating the finger subjected to the contour extraction, and FIG. 18(b) is a view illustrating the finger subjected to the rotation correction.

The operation of the authentication is performed through the calculation of correlation to find a similarity between a blood vessel pattern image of the finger registered in advance and a blood vessel pattern image of the finger captured by the imaging unit. An authentication result is obtained by performing a threshold processing for the value obtained by the correlation calculation.

CITATION LIST

[Patent Literature]
PTL 1: JP-P2002-92616A

SUMMARY OF INVENTION

Technical Problem

The technically problematic point of the above-mentioned Patent literature 1 is that the time for obtaining the authentication result is lengthy. That is, the foregoing art necessitates the rotation processing in order to obtain the authentication result. The processing time of this rotation processing is long because it demands a large arithmetic amount.

Upon explaining more detailedly, the personal identification system of the Patent literature 1 performs the contour extraction for the image acquired by the image acquiring unit, and performs the rotation processing for the image by using the position information of the contour. Although there are various techniques as this rotation processing of the image, any technique demands a large arithmetic amount.

The affine transform is a representative example of the image rotation processing. The affine transform, which is a technique obtained by synthesizing a primary transform and a movement, performs the rotation processing of the image. Rotating the image with the affine transform necessitates obtaining coordinates of the corresponding pixels in the before-rotation image and the after-rotation image, and the method of applying coordinate transformation matrix exists. Applying the coordinate transformation matrix per one pixel yields the following.

$$\begin{pmatrix} x' \\ y' \end{pmatrix} = \begin{bmatrix} \alpha & \beta \\ \chi & \delta \end{bmatrix} \begin{pmatrix} x \\ y \end{pmatrix}$$

This arithmetic operation necessitates performing product computation four times and sum computation twice, respectively. Applying the coordinate transformation matrix for the image of which the number of the pixels is N necessitates performing the product computation 4×N times and the sum computation 2×N, respectively. Hence, the computational complexity becomes very much. That is, the Patent literature 1 has a problem that the processing time becomes lengthy because a large computation complexity is required for the rotation correctness.

Thus, the problem that is to be resolved by the present invention is resolved by providing an image collating technology capable of obtaining the authentication result in a short time period.

Solution to Problem

The present invention for solving the above-mentioned problems is a collating device for collating an image that is characterized in including a reference line extracting unit for extracting a predetermined reference line in the image, an image correcting unit for correcting the image by moving it for each partial image so that the reference line acquired by the foregoing reference line extracting unit becomes a pre-decided one, and an image collating unit for collating the image corrected by the foregoing image correcting unit with a predetermined image.

The present invention for solving the above-mentioned problems is a collating method of collating an image that is characterized in including a reference line extracting step of extracting a predetermined reference line in the image, an image correcting step of correcting the image by moving it for each partial image so that the reference line acquired by the foregoing reference line extracting step becomes a pre-decided one, and a collating step of collating the image corrected by the foregoing image correcting step with a predetermined image.

The present invention for solving the above-mentioned problems is a program for causing the collating device to execute a reference line extracting process of extracting a predetermined reference line in the image, an image correcting process of correcting the image by moving it for each partial image so that the reference line acquired by the foregoing reference line extracting process becomes a pre-decided one, and a collating process of collating the image corrected by the foregoing image correcting process with a predetermined image.

The present invention for solving the above-mentioned problems is a correcting device that is characterized in including a reference line extracting unit for extracting a predetermined reference line in the image, and an image correcting unit for correcting the image by moving it for each partial image so that the reference line acquired by the foregoing reference line extracting unit becomes a pre-decided one.

The present invention for solving the above-mentioned problems is a correcting method that is characterized in including a reference line extracting step of extracting a predetermined reference line in the image and an image correcting step of correcting the image by moving it for each partial image so that the reference line acquired by the foregoing reference line extracting step becomes a pre-decided one.

The present invention for solving the above-mentioned problems is a program for causing the correcting device to execute a reference line extracting process of extracting a predetermined reference line in the image, and an image correcting process of correcting the image by moving it for each partial image so that the reference line acquired by the foregoing reference line extracting process becomes a pre-decided one.

Advantageous Effect of Invention

The authentication result of the image can be obtained in a short time period. That is, the present invention allows the image to be corrected by moving it for each partial image. And, the image rotation processing that demands a long time for the processing is eliminated, and the processing time required for the image correction is shortened.

DESCRIPTION OF EMBODIMENTS

Figure 1:
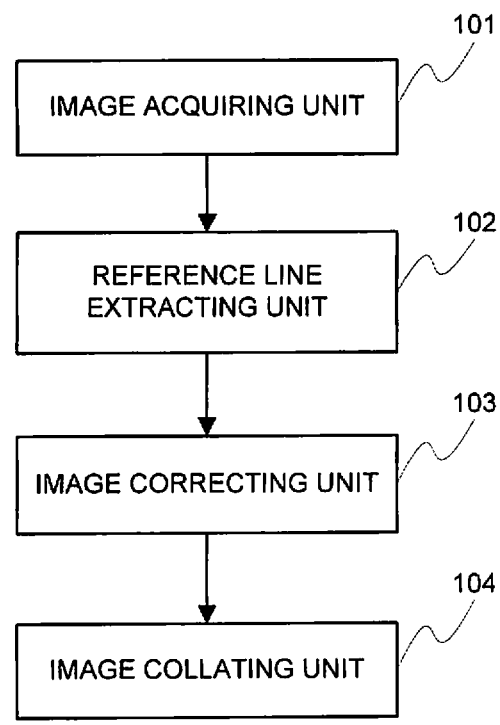
FIG. 1 is a block diagram of the collating device in accordance with a first exemplary embodiment of the present invention.

The present invention is a collating device. In particular, the present invention is a collating device for collating the image. For example, the present invention is a collating device for collating the image of the living body such as a finger, a palm, and a face. This collating device includes a reference line extracting unit for extracting a predetermined reference line in the image. Yet, the collating device includes an image correcting unit (device) for correcting the image by moving it for each partial image so that the reference line acquired by the foregoing reference line extracting unit becomes a pre-decided one (for example, a pre-decided line (for example, a straight line), a line having a pre-decided position, or a line having a pre-decided shape). Preferably, the collating device includes an image correcting unit (device) for, with the width of a one-pixel portion defined as one line, and the image comprised of at least one line defined as a partial image, correcting the image by translating it for each this partial image so that the reference line acquired by the foregoing reference line extracting unit (device) becomes a pre-decided one (for example, a pre-decided line (for example, a straight line), a line having a pre-decided position, or a line having a pre-decided shape). In addition, the collating device includes an image collating unit (device) for collating the image corrected by the foregoing image correcting unit (device) with a predetermined image (for example, the already registered image stored in a storing unit (device)). The foregoing reference line extracting unit is a device for exacting the centerline (or contour line) of the image. The foregoing reference line extracting unit preferably includes a binarizing unit (device) for extracting one region or plural regions by binarizing the image, a minute-region removing unit (device) for extracting the region having a maximum area in the region extracted by the foregoing binarizing unit, and a centerline extracting unit (device) for extracting the centerline from the region extracted by the foregoing minute-region removing unit. The foregoing reference line extracting unit preferably includes a centerline correcting unit (device) for correcting the centerline on the basis of the line equivalent to the maximum length when the centerline extracted by the foregoing centerline extracting unit is comprised of, for example, two lines or more. The foregoing reference line extracting unit preferably includes a centerline correcting unit (device) for, when an averaged value of the coordinates of the center points within a certain scope, which extends ahead of and behind a certain center point, exceeds a threshold, correcting the centerline extracted by the foregoing centerline extracting unit by removing the above center point and changing the coordinate of this removed center point to an average value of the coordinates of the remaining center points. The foregoing reference line extracting unit can be also configured to adopt not the centerline but the contour line as the reference line. Additionally, when the contour line is used as the reference line, the so-called contour line is at least one part of the contour line. More preferably, it is one part of the contour line. From among, it is the contour line within a specific partial region decided for each target of the image. In such a case, the reference line extracting unit includes a binarizing unit (device) for extracting one region or plural regions by binarizing the image, a minute-region removing unit (device) for extracting the region having a maximum area in the region extracted by the foregoing binarizing unit, and a contour line extracting unit (device) for extracting the contour line from the region extracted by the foregoing minute-region removing unit. The foregoing reference line extracting unit preferably includes a contour line correcting unit (device) for correcting the contour line on the basis of the line equivalent to the maximum length when the contour line extracted by the foregoing contour line extracting unit is comprised of, for example, two lines or more. The foregoing reference line extracting unit preferably includes a contour line correcting unit (device) for, when an averaged value of the coordinates of the contour points within a certain scope, which extends ahead of and behind a certain contour point, exceeds a threshold, correcting the contour line extracted by the foregoing contour line extracting unit by removing the above contour point and changing the coordinate of this removed contour point to an average value of the coordinates of the remaining contour points. Various technologies can be adopted for the foregoing image collating unit. For example, the image collating unit including a device for performing a Fourier transform line by line, a device for extracting a main component of the features by each partial image by performing a linear transform for Fourier amplitude spectra obtained by the foregoing Fourier transform, and a device for computing a similarity with a dynamic programming matching operation by using the main component of the features obtained by the foregoing linear transform can be listed as a preferred one. Herein, the so-called one line is a width of a one-pixel portion. Additionally, as the preferred device for extracting the main component of the features by each partial image, one including a storing device having basis matrixes stored therein that have been obtained by performing a main component analysis for a learning image set, and a device for obtaining the main component by performing a linear transform for the image by using the foregoing stored basis matrixes can be listed.

The present invention is a collating method. In particular, the present invention is a collating method of collating the image. For example, the present invention is a collating method of collating the image of the living body such as the finger, the palm, and the face. From among, it is a collating method using the foregoing collating device. The foregoing collating method includes a reference line extracting step of extracting a predetermined reference line in the image. Further, the collating method includes an image correcting step of correcting the image by moving it for each partial image so that the reference line acquired by the foregoing reference line extracting step becomes a pre-decided one (for example, a pre-decided line (for example, a straight line), a line having a pre-decided position, or a line having a pre-decided shape). Further, the collating method includes a collating step of collating the image corrected by the foregoing image correcting step with a predetermined image. The foregoing reference line extracting step is a step of exacting the centerline (or contour line) of the image. This reference line extracting step preferably includes a binarizing step of extracting one region or plural regions by binarizing the image, a minute-region removing step of extracting the region having a maximum area from region extracted by the foregoing binarizing step, and a centerline extracting step of extracting the centerline from the region extracted by the foregoing minute-region removing step. The reference line extracting step preferably includes a centerline correcting step of correcting the centerline on the basis of the line equivalent to the maximum length when the centerline extracted by the foregoing centerline extracting step is comprised of, for example, two lines or more. Or, the foregoing reference line extracting step preferably includes a step of, when an averaged value of the coordinates of the center points within a certain scope, which extends ahead of and behind a certain center point, exceeds a threshold, correcting the centerline extracted by the foregoing centerline extracting step by removing the above center point and changing the coordinate of this removed center point to an average value of the coordinates of the remaining center points. The foregoing reference line extracting step can also adopt not the centerline but the contour line as the reference line. Additionally, when the contour line is used as the reference line, the so-called contour line is at least one part of the contour line. More preferably, it is one part of the contour line. From among, it is the contour line within a specific partial region decided for each target of the image. In such a case, the reference line extracting step preferably includes a binarizing step of extracting one region or plural regions by binarizing the image, a minute-region removing step of extracting the region having a maximum area in the region extracted by the foregoing binarizing step, and a contour line extracting step of extracting the contour line from the region extracted by the foregoing minute-region removing step. The reference line extracting step preferably includes a step of correcting the contour line by deciding the contour line on the basis of the line equivalent to the maximum length when the contour line extracted by the foregoing contour line extracting step is comprised of two lines or more. Or, the reference line extracting step preferably includes a step (a step of correcting the contour line) of, when an averaged value of the coordinates of the contour points within a certain scope, which extends ahead of and behind a certain contour point, exceeds a threshold, removing the above contour point, and changing the coordinate of this removed contour point to an average value of the coordinates of the remaining contour points with regard to the contour line extracted by the foregoing contour line extracting step. Various technologies can be adopted for the above-mentioned collating step. For example, the collating step including a step of performing a Fourier transform line by line, a step of extracting a main component of the features by each foregoing partial image by performing a linear transform for Fourier amplitude spectra obtained by the foregoing Fourier transform, and a step of computing a similarity with a dynamic programming matching operation by using the main component of the features obtained by the foregoing linear transform can be listed as a preferred one. Additionally, as the preferred step of extracting the main component of the features by each partial image, one including a step of obtaining the main component by performing the linear transform for the image using the basis matrix obtained by performing a main component analysis for a learning image set can be listed.

The present invention is a program. In particular, the present invention is a program for causing the foregoing collating device to execute various processes. Or it is a program for causing the foregoing collating device to execute the foregoing steps.

While the collating device of the present invention can be also configured of hardware, it can be also realized with a computer program.

The program of the present invention includes a reference line extracting process of extracting a predetermined reference line in the image. Further, the program includes an image correcting process of correcting the image by moving it for each partial image so that the reference line acquired by the foregoing reference line extracting process becomes a pre-decided one (for example, a pre-decided line (for example, a straight line), a line having a pre-decided position, or a line having a pre-decided shape). Further, the program includes a collating process of collating the image corrected by the foregoing image correcting process with a predetermined image. The foregoing reference line extracting process is a process of exacting the centerline (or contour line) of the image. This reference line extracting process preferably includes a binarizing process of extracting one region or plural regions by binarizing the image, a minute-region removing process of extracting the region having a maximum area from region extracted by the foregoing binarizing process, and a centerline extracting process of extracting the centerline from the region extracted by the foregoing minute-region removing process. The foregoing reference line extracting process preferably includes a centerline correcting process of correcting the centerline on the basis of the line equivalent to the maximum length when the centerline extracted by the foregoing centerline extracting process is comprised of, for example, two lines or more. Or, the foregoing reference line extracting process preferably includes a process of, when an averaged value of the coordinates of the center points within a certain scope, which extends ahead of and behind a certain center point, exceeds a threshold, correcting the centerline extracted by the foregoing centerline extracting process by removing the above center point and changing the coordinate of this removed center point to an average value of the coordinates of the remaining center points. Or, the foregoing reference line extracting process can also adopt not the centerline but the contour line as the reference line. Additionally, when the contour line is used as the reference line, the so-called contour line is at least one part of the contour line. More preferably, it is one part of the contour line. From among, it is the contour line within a specific partial region decided for each target of the image. In such a case, the reference line extracting process preferably includes a binarizing process of extracting one region or plural regions by binarizing the image, a minute-region removing process of extracting the region having a maximum area in the region extracted by the foregoing binarizing process, and a contour line extracting process of extracting the contour line from the region extracted by the foregoing minute-region removing process. The foregoing reference line extracting process preferably includes a process of correcting the contour line by deciding the contour line on the basis of the line equivalent to the maximum length when the contour line extracted by the foregoing contour line extracting process is comprised of two lines or more. Or, the reference line extracting process preferably includes a process of, when an averaged value of the coordinates of the contour points within a certain scope, which extends ahead of and behind a certain contour point, exceeds a threshold, correcting the contour line extracted by the foregoing contour line extraction process by removing the above contour point and changing the coordinate of this removed contour point to an average value of the coordinates of the remaining contour points. Various technologies can be adopted for the above-mentioned collating process. For example, the collating process including a process of performing a Fourier transform line by line, a process of extracting a main component of the features by each foregoing partial image by performing a linear transform for Fourier amplitude spectra obtained by the foregoing Fourier transform, and a process of computing a similarity with a dynamic programming matching operation by using the main component of the features obtained by the foregoing linear transform can be listed as a preferred one. Additionally, as the process of extracting the main component of the features by each partial image, one including a process of obtaining the main component by performing the linear transform for the image using the basis matrix obtained by performing a main component analysis for a learning image set can be preferably listed.

In the present invention, the following coordinate transform is performed at the moment of obtaining the coordinates of the corresponding pixels that correspond to the before-correction and after-correction images.

$$y = y' + \epsilon$$

The coordinate transform of the pixel in the present invention is one-directionally performed. The number of the coordinate values of the pixel is two because the image is two-dimensional, but the number of the coordinates associated with the coordinate transform is one (1). Thus, the processing required for the coordinate transform is finished with the one-time sum computation. When the coordinate transform is applied for the image of which the number of the pixels is N, the processing is finished with the N-time sum computation. On the other hand, when the coordinate transform in the image rotation processing is applied for the image of which the number of the pixels is N, it is necessary to perform the product computation 4×N times, and the sum computation 2×N times. Thus, the present invention allows the computational complexity required for the image correction to be drastically reduced. Hence, a reduction in the processing time can be realized. Namely, performing the image correction by each partial image as mentioned above makes it possible to omit the rotation processing of the image. And, the processing time required for correcting the image is shortened.

Hereinafter, the present invention will be explained yet specifically.

FIG. 1 is a block diagram of the collating device of the first exemplary embodiment of the present invention.

The collating device of the present invention includes an image acquiring unit 101, a reference line extracting unit 102, an image correcting unit 103, and an image collating unit 104. The image acquiring unit 101 is a device for acquiring the image, being an imaging target. The reference line extracting unit 102 is a device for extracting the reference line from the image acquired by the image acquiring unit 101. The image correcting unit 103 is a device for perform the position correction of the image based upon the reference line extracted by the reference line extracting unit 102. The image collating unit 104 is a device for collating the image corrected by the image correcting unit 103 with a predetermined image (already registered image).

Figure 2:
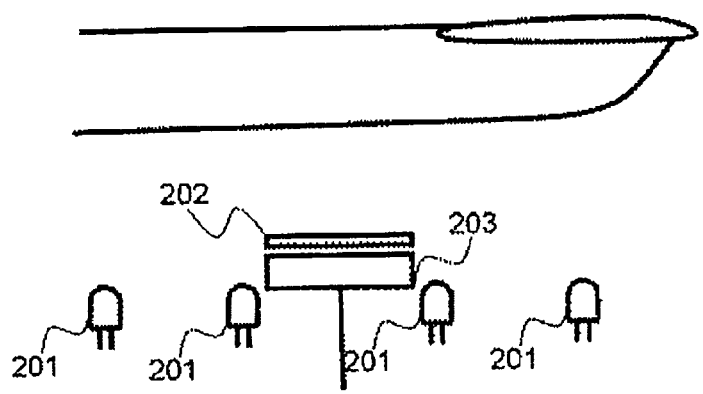
FIG. 2 is a schematic drawing of an image acquiring unit in the first exemplary embodiment of the present invention.

The image acquiring unit 101 includes, for example, near-infrared LEDs 201, an infrared transparent filter 202, an imaging device 203 (see FIG. 2). Additionally, in FIG. 2, the portion (finger-shaped portion) depicted in the utmost top is a imaging target.

The near-infrared LED 201 is used as a light source for illumination at the moment of capturing the image of the imaging target. The near-infrared LEDs 201 are arranged in a side identical to that of the imaging device 203 with the imaging target taken as a reference. Arranging the near-infrared LEDs 201 in such a manner allows light reflected mainly at a skin surface to be observed. And, the image of the surface pattern of the imaging target is captured. Such an imaging method (the method of arranging the light source in a side identical to that of the imaging device 203 with the imaging target taken as a reference, and observing the reflected light) is called a reflected light sensing.

In the present invention, as the imaging target, in particular, the portions such as the finger, the palm, and the face can be listed. Additionally, from now on, the personal authentication in the case of using the finger as the imaging target will be explained basically. However, the situation is similar with a case of applying for the palm and the face.

A fingerprint exists on the surface of the finger. The fingerprint has a ridge (a projected portion on the skin surface) and a recess (hollowed portion). In the ridge portion of the finger, the thickness of the skin surface is thick, and blood flowing into the blood vessel is hardly observed. And, in the surface of the ridge portion of the finger, the captured image is bright because the amount of diffused reflection and specular reflection becomes much. In the recess portion of the finger, the thickness of the skin surface is thin, and the amount of light permeating into dermis under the skin surface, in which the blood vessel exists, is much. And, in the recess portion of the finger, the captured image is dark because absorption of light is much, diffused reflection is much and specular reflection is few. From such a background, the near-infrared LEDs 201 are arranged so that the light amount of the specular reflection becomes much in order to suppress unevenness of illumination caused by a localized shape of the finger.

The infrared transparent filter 202 is an infrared transparent filter (IR filter) that passes, for example, near-infrared ray with a wavelength of 700 to 900 nm. Using the IR filter makes it difficult to pass light having a wavelength shorter than the limited wavelength that is decided based upon a filter feature. As a result, an influence of the turbulence light such as room illumination and sunshine can be reduced.

The infrared transparent filter 202 is installed in a lens unit of the imaging device 203 (see FIG. 2). Additionally, the infrared transparent filter 202 may be arranged between the near-infrared LEDs 201 and the imaging device 203, and an imaging target (finger) instead of installing the infrared transparent filter 202 in the lens unit of the imaging device 203, partly because of protecting the near-infrared LEDs 201 and the imaging device 203.

The imaging device 203 includes a two-dimensional imaging element (for example, a CCD sensor or a CMOS sensor) and a lens. Preferably, the two-dimensional imaging element is an element having resolution matched to the living body of which image is captured. When image of the portion ranging from the middle phalanx of the finger to fingertip is captured at approximate 500 dpi, for example, the element of 1.3 million pixels having 1280×1024 pixels is used.

The followings proceed so as to acquire the image of the imaging target by using the above-mentioned image acquiring unit (device) 101.

At first, the near-infrared LEDs 201 are illuminated, and the image of the imaging target is captured by the imaging device 203.

Figure 3:
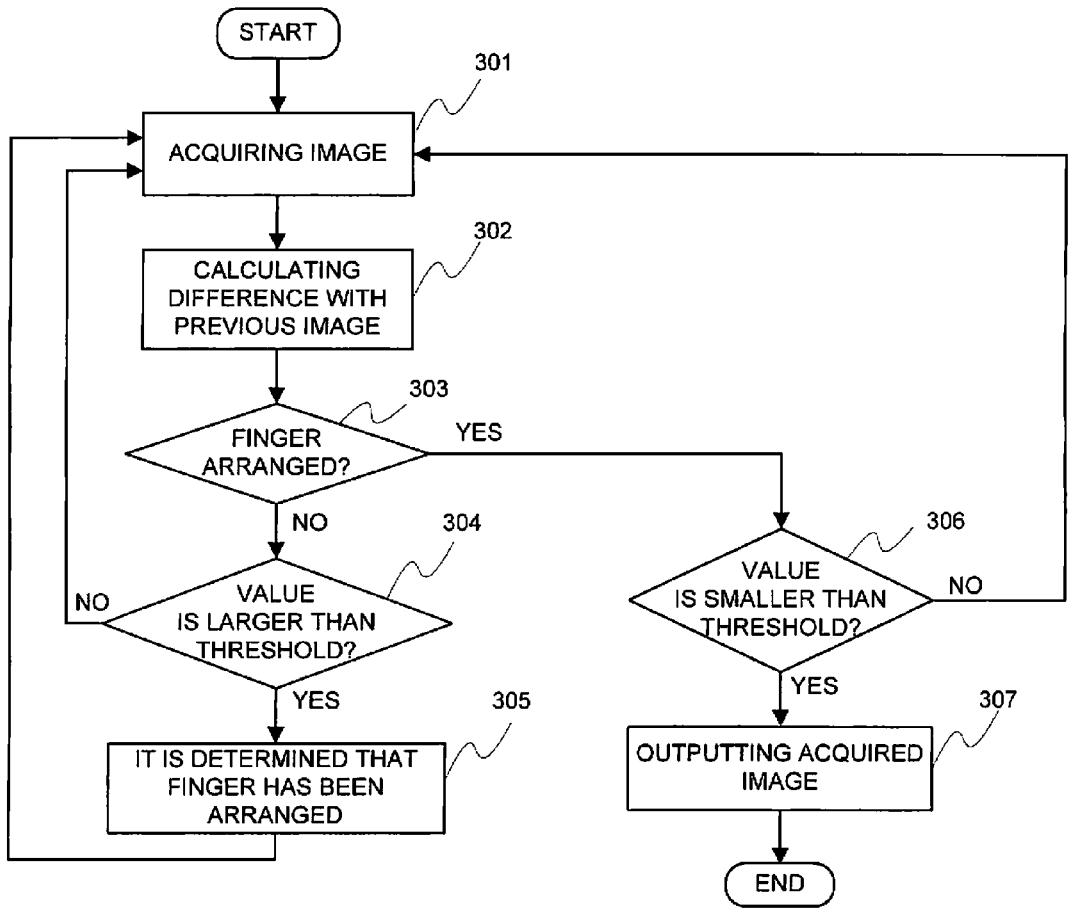
FIG. 3 is a flowchart of the image acquisition in the first exemplary embodiment of the present invention.

It is determined according to a flow shown in FIG. 3 whether the image is acquired.

In a step 301 (acquiring the image), the image is acquired by the imaging device.

In a step 302 (calculating a difference with the previous image), a total sum of the difference of the image between last-time image and this-time image for the frames is calculated.

In a step 303 (the finger arranged?), a value of a status flag for keeping information as to whether or not the finger has been arranged is determined. With the status in which the finger has not been arranged, the operation proceeds to a step 304 (the total sum is larger than a threshold?). And, it is determined whether or not the calculated total sum of the difference between the images is larger than a threshold. When it is larger than a threshold, it is determined that the imaging target has been placed. That is, in a step 305 (it is determined that the finger has been placed), the status flag is updated. Thereafter, the operation returns to the step 301, the image is re-acquired, and a total sum of the difference with the previous image is calculated.

On the other hand, with the status in which the finger has been arranged, it is determined in a step 306 (the total sum is smaller than a threshold?) whether or not the total sum of the difference is larger than a threshold. When it is smaller than a threshold, the operation proceeds to a step 307 (outputting the acquired image) by determining that no movement of the finger exists. And, the image acquired at this time is outputted. When it is larger than a threshold, the operation returns to the step 301, and the image is re-acquired.

The reference line extracting unit 102 extracts the reference line, being a reference of the image correction, from image of the imaging target acquired by the image acquiring unit 101. The extracted reference line is founded upon the features of the living body, being a target. For example, with the case that the living body, being a target, is the finger, a specific line that is decided based upon the centerline (or, the contour line or both of the centerline and the contour line) of the finger. With the case that the living body is the face, for example, the bridge of the nose passing through the middle of the eyebrows and the nose tip is defined as the reference line.

Hereinafter, the case that the centerline is extracted as the reference line of the finger will be explained. Additionally, the centerline is centrally positioned from a boundary (contour).

Figure 4:
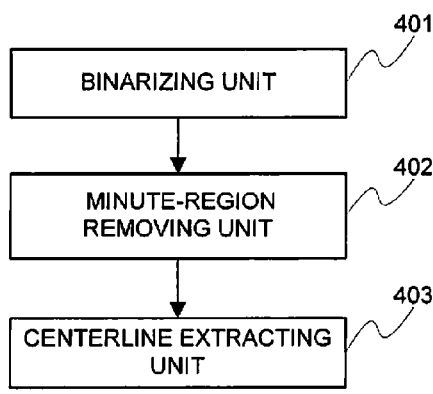
FIG. 4 is a block diagram of a reference line extracting unit in the first exemplary embodiment of the present invention.

The reference line extracting unit 102 of this exemplary embodiment includes a binarizing unit 401, a minute-region removing unit 402, and a centerline extracting unit 403 (see FIG. 4). The binarizing unit 401 is a device for performing a binarization processing for the image of the imaging target acquired by the image acquiring unit 101. The minute-region removing unit 402 is a device for removing minute regions from the image binarized by the binarizing unit 401, and extracting the region (maximum region) of the finger. The centerline extracting unit 403 is a device for extracting the centerline of the above region from the region (maximum region) of the finger extracted by the minute-region removing unit 402.

Next, an operation for extracting the reference line from the image acquired by the image acquiring unit 101 will be explained.

The binarizing unit 401 performs a threshold processing for the image acquired by the image acquiring unit 101. This allows the image to be binarized. The image acquired by the image acquiring unit 101 is an image captured by the imaging device 203 as a result of the near-infrared ray emitted from the near-infrared LEDs 201 being reflected at the finger. Thus, in the acquired image, the region in which the finger exists is bright (the pixel value is large). On the other hand, in the acquired image, the region in which no finger exists is dark because the near-infrared ray is not reflected and yet an influence of the turbulence light such as room illumination and sunshine is reduced by the infrared transparent filter 202. In such a manner, in the acquired image, the region of the finger becomes a region having a large pixel value and the region in which no finger exists becomes a region having a small pixel value. The binarizing unit 401, which aims for extracting the region equivalent to the finger, binarizes the image with the decided threshold defined as a reference so that the region of the finger and the background are separated excellently.

The minute-region removing unit 402 removes the minute regions (not the region of the finger) to be included in the image binarized by the binarizing unit 401. The image (the region having a large pixel value different from that of the finger) caused by the noise and the background exists in the images acquired by the image acquiring unit 101 in some cases. The binarizing unit 401 resultantly extracts, as the region of the finger, such a region as well. Thereupon, the minute-region removing unit 402 obtains respective areas of a plurality of the regions existing in the binarized image. The minute-region removing unit 402 selects the region having a maximum area from among them, and extracts the region having a maximum area as the region of the finger. The reason why the region having a maximum area is extracted as the region of the finger is that it can be estimated that the region having a maximum area existing in the image is the region of the finger because the region of the finger occupies the majority of the area of the image captured by the image acquiring unit 101. In such a manner, the minute-region removing unit 402 can extract the region of the finger from the regions obtained by the binarizing unit 401.

The centerline extracting unit 403 extracts the centerline of the finger as the reference line from the regions of the finger extracted by the minute-region removing unit 402.

Figure 5:
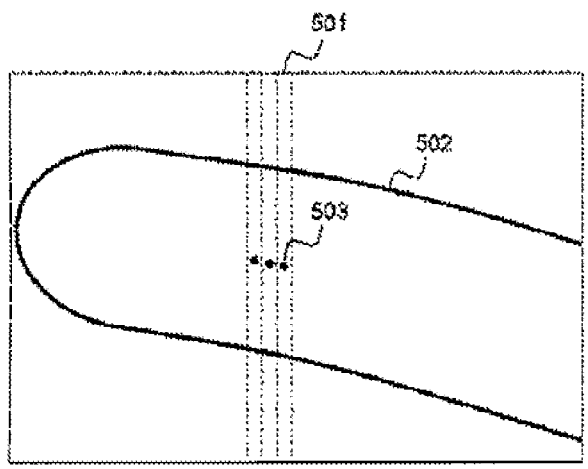
FIG. 5 is an explanatory view illustrating an example of extracting the centerline in the first exemplary embodiment of the present invention.

With regard to the finger existing in the image, the axis along a direction from the root of the finger toward the finger tip is defined as a longitudinal axis, and the axis orthogonal to this longitudinal axis is defined as a lateral axis. Herein, the coordinates of the center points are extracted for each partial image in the lateral direction on the assumption that centerline to be extracted by the centerline extracting unit 403 is along the longitudinal axis. Herein, the center point is centrally positioned from a boundary (contour). For example, in the case that, with the partial image having a width of a one-pixel portion defined as one line, the center point is extracted one line by one line, the processing is performed as follow (see FIG. 5). The centerline extracting unit 403 scans one line of the edge of the image in the lateral direction (in FIG. 5, the vertical direction), and investigates the coordinates of both edge points of the region of the finger within the line. The centerline extracting unit 403 defines the central coordinate of the acquired coordinates of both edge points as the center point of the finger in this line. The centerline extracting unit 403 sequentially updates the line along the longitudinal direction (in FIG. 5, the horizontal direction), and investigates the center points of the fingers in all of the lines. It extracts the centerline of the region of the finger in such a manner.

When the center point of the region of the finger is extracted for every plural lines with the partial image defined as the image of a plurality of the lines, the center point is extracted, for example, with the following processing. The centerline extracting unit 403, similarly to the method of extracting the center point one line by one line, extracts the center point for each line within the plural lines. And, the centerline extracting unit 403 defines an averaged value of the coordinates of the center points extracted for each one line within a plurality of the lines as the center point within plural lines. The centerline extracting unit 403 extracts the center point of the region of the finger for every plural lines by sequentially updating the plural lines along the longitudinal direction, and extracting respective center points.

The image correcting unit 103 performs the position correction for the image of the imaging target acquired by the image acquiring unit 101 by using the reference line extracted by the reference line extracting unit 102. By the way, the reference line extracted by the reference line extracting unit 102 is inclined or crooked in some cases. The reason is that the imaging target (finger) is inclined or crooked in some cases when the image is acquired by the image acquiring unit 101.

Figure 6:
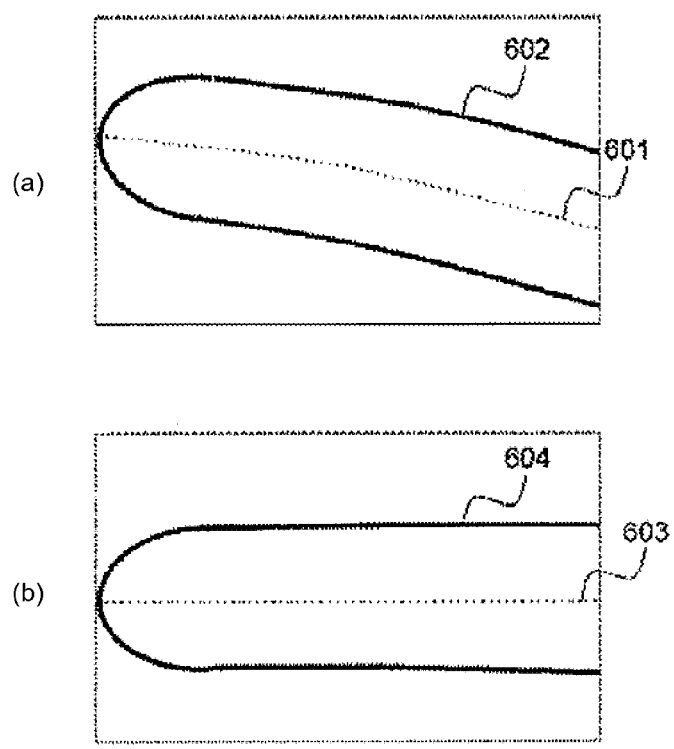
FIG. 6 is an explanatory view illustrating an example of correcting the image in the first exemplary embodiment of the present invention.

Thereupon, the image correcting unit 103 translates the image for each partial image in the lateral direction so that the centerline acquired by the reference line extracting unit 102 becomes a pre-decided line, for example, a straight line that is horizontal with respect to the left direction and the right direction (see FIG. 6). The image correcting unit 103 outputs the image moved in such a manner as the after-correction image. Additionally, FIG. 6(a) is a view illustrating the before-correction finger region and its centerline. FIG. 6(b) is a view illustrating the after-correction finger region and its centerline.

And, performing the image correction for each partial image makes it possible to curtail the arithmetic amount all the more as compared with the case of applying the rotation processing for the image. Thus, the fast image correction can be realized.

Figure 7:
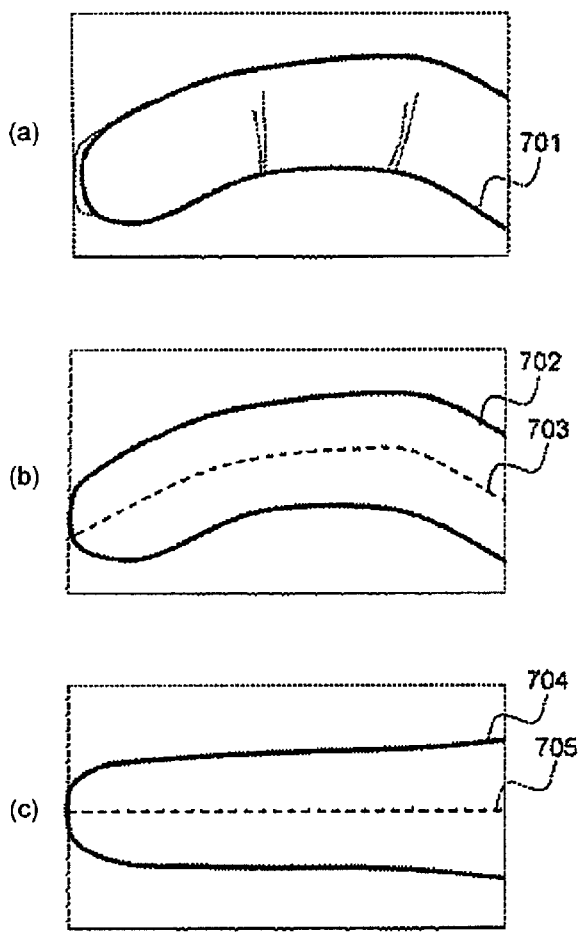
FIG. 7 is an explanatory view illustrating an effect of the image correction upon the curved living body in the first exemplary embodiment of the present invention.

It is also possible to correct the crooked image (see FIG. 7). For example, the finger has a joint. The image is easily crooked because the finger is bent at this joint. The image of the crooked finger is shown in FIG. 7(a). In the rotation processing of the image, the crooked image is rotated without a modification to the shape. Thus, it is impossible to correct the crookedness by the rotation processing. For this, when one, out of the images acquired from the identical living body, is crooked at the moment of collating the images, a collation result declines. On the other hand, the present invention is capable of correcting the crooked image because each partial image is corrected based upon the reference line (see FIGS. 7(b) and (c)). FIG. 7(b) shows the before-correction finger region and its centerline. FIG. 7(c) shows the after-correction finger region and its centerline.

The image collating unit 104 performs the collation by using the after-correction image outputted by the image correcting unit 103.

Next, the details of the image collating unit 104 will be explained.

Figure 8:
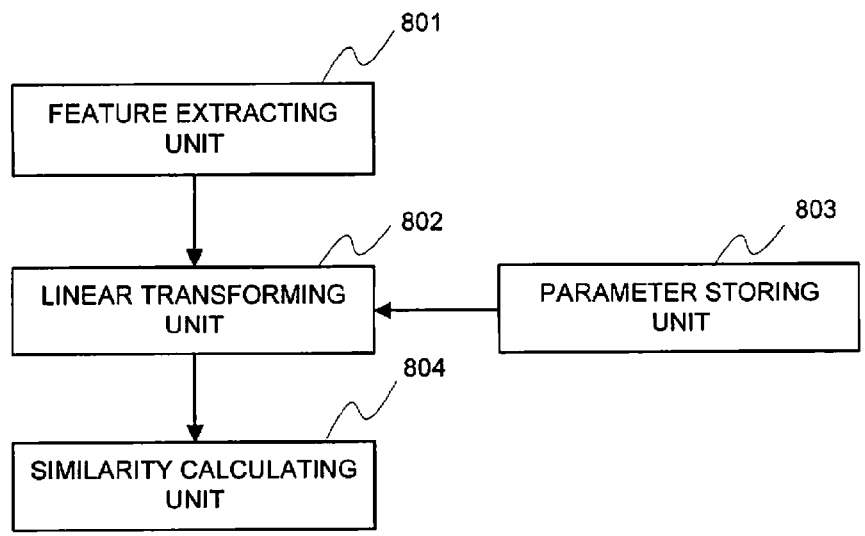
FIG. 8 is a block diagram illustrating an image collating unit in the first exemplary embodiment of the present invention.

A block diagram of the image collating unit (device) 104 is shown (see FIG. 8).

The image collating unit 104 includes a feature extracting unit 801, a linear transforming unit 802, a parameter storing unit 803, and a similarity calculating unit 804. The feature extracting unit 801 is a device for extracting the features to be used for the collation from image corrected by the image correcting unit 103. The linear transforming unit 802 is a device for performing a linear transform for the features extracted by the feature extracting unit 801. The parameter storing unit 803 is a device having parameters to be used for the linear transforming unit 802 stored therein. The similarity calculating unit 804 is a device for calculating a similarity by using the value acquired by linear transforming unit 802.

The feature extracting unit 801 extracts the features. With the case that the imaging target is the finger, the feature is one-dimensional Fourier amplitude spectra in the lateral direction of a surface pattern of the finger (or a pattern of the blood vessel of the finger such as the finger vein) that is typified by the fingerprint. At first, the feature extracting unit 801 calculates the Fourier amplitude spectra to be acquired by a one-dimensional discrete Fourier transform line by line with regard to the lateral direction of after-correction image. Thereafter, the feature extracting unit 801 removes components unnecessary for the determination such as direct components, and symmetric components of the Fourier amplitude spectra, taking into consideration the fact that the Fourier amplitude spectra are symmetric, and extracts the features valid for determination.

The linear transforming unit 802 extracts a main component of the features acquired by the feature extracting unit 801. The main component is extracted by using basis matrix stored in the parameter storing unit 803, and performing a linear transform for the features extracted by the feature extracting unit 801. The basis matrixes stored in the parameter storing unit 803 are ones obtained in advance by performing the main component analysis for the specially prepared learning set. The main component analysis is one of the techniques of realizing dimensional reduction of data while minimizing the information loss amount.

The similarity calculating unit 804 performs a matching, which takes position drift and distortion as to one direction into consideration, for the features of the main component acquired by the linear transforming unit 802 by using a DP matching method (dynamic programming matching method). In the DP matching method, the distance of the DP matching at the time that a distance between two features becomes minimized is calculated as a similarity between two features. The similarity is acquired as the distance of the DP matching, whereby the smaller the acquired value, higher the similarity. The above-mentioned technique is called a frequency DP matching method.

Next, the second exemplary embodiment obtained by altering the above-mentioned first embodiment will be explained.

In this exemplary embodiment, the imaging target is the palm. The second exemplary embodiment differs from the first exemplary embodiment in this point. And, the image acquiring unit (device) of this exemplary embodiment includes a palm guide for efficiently capturing the image of the palm in addition to a configuration of the first exemplary embodiment.

Similarly to the finger in which the fingerprint and the finger vein exist, there exist a palm print and a palm vein in the palm. Similarly to the fingerprint, the palm print as well has the ridge and the recess. And, in the acquired image, the ridge is bright because the reflection of light is much, and the recess is dark because the absorption of light is much.

Figure 9:
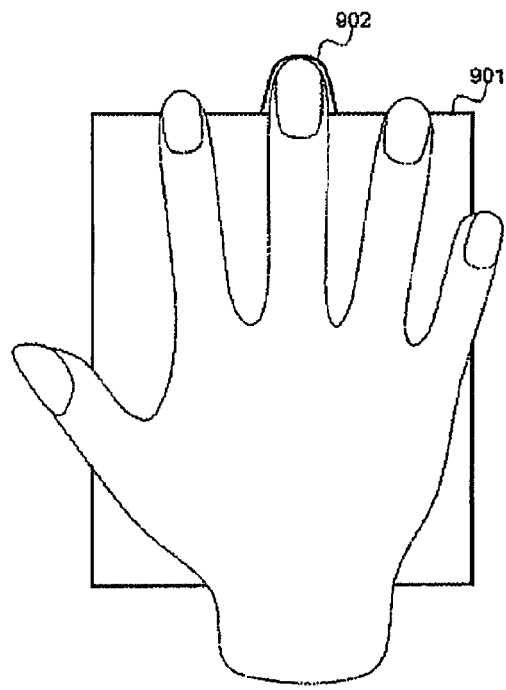
FIG. 9 is an explanatory view of the image acquiring unit in a second exemplary embodiment of the present invention.

The above-mentioned palm guide is shown in FIG. 9.

The palm guide includes an imaging scope guide 901 and a second finger guide 902.

The finger is arranged to the second finger guide 902 at the moment of capturing the image of the palm. And, the hand is opened, the thumb and the little finger are placed in both sides of the imaging scope guide 901, the forefinger and the ring finger are placed in a side identical to that of the second finger (see FIG. 9). Capturing the image of the palm arranged in such a manner allows a scope beyond the wrist to be acquired as the image. Using the palm guide as mentioned above makes it possible to roughly decide the position of the palm within the acquired image.

Hereinafter, the axis along a direction from the wrist toward the second finger is defined as a longitudinal axis of the palm, and the axis orthogonal to this longitudinal axis is defined as a lateral axis of the palm.

Next, an operation for extracting the reference line from the image of the palm acquired by the image acquiring unit (device) will be explained.

The reference line extracting unit of the palm has a configuration similar to that of the reference line extracting unit used for the finger (see FIG. 4).

The binarizing unit 401 binarizes the image by the threshold processing having the pixel value of the acquired image as a reference. This allows the region of the palm to be extracted.

The minute-region removing unit 402 removes the minute regions (the region different from the region of the palm) included in the image binarized by the binarizing unit 401.

The centerline extracting unit 403 extracts the reference line from the region of the palm extracted by the minute-region removing unit 402. With the palm, it is difficult to extract the centerline with a method similar to that of the finger because of an influence of the thumb or the like. Thereupon, it is favorable to use, for example, the line obtained by extending the centerline of the second finger as the reference line of the palm. The reason is that the second finger, out of the five fingers, has a relatively straight-line shape, and the extended line of the centerline of the second finger almost coincides with the centerline in the lateral direction of the palm.

Figure 10:
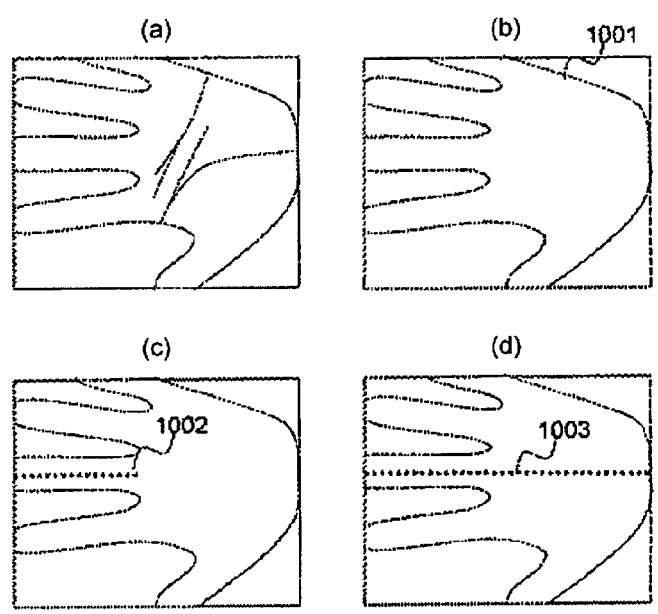
FIG. 10 is an explanatory view of an example of extracting the reference line in the second exemplary embodiment of the present invention.

Next, an example of extracting the reference line of the palm is shown in FIG. 10. FIG. 10(*a*) shows the image of the palm. FIG. 10(*b*) shows the image in which the minute regions have been removed. FIG. 10(*c*) shows the image in which the centerline of the second finger has been extracted. FIG. 10(*d*) shows the image in which the centerline of the palm has been extracted.

The processing of the binarizing unit 401 and the minute-region removing unit 402 are applied (see FIG. 10(*b*)) for the image acquired by the image acquiring unit 101 (see FIG. 10(*a*)). As mentioned above, with regard to the image of the palm acquired by the image acquiring unit 101, the position of the second finger thereof is roughly is decided by the palm guide 901 of the image acquiring unit 101. Thereupon, the region of the second finger is decided from among the image in which the minute regions have been removed at a fixed position. And, the processing of the centerline extracting unit 403 is applied for the second finger. This allows the centerline of the second finger to be extracted (see FIG. 10(*c*)). The centerline of the second finger extracted by the centerline extracting unit 403 is extended, and the extended line is defined as the centerline of the palm (see FIG. 10(*d*)).

The image correcting unit 103 performs the image correction for the image of the palm acquired by the image acquiring unit 101 by using the reference line extracted by the reference line extracting unit 102.

The extracted reference line of the palm is inclined due to the rotation and position drift of the hand and the like in some cases. Thereupon, the image is translated for each partial image in the lateral direction with the processing similar to that of the finger so that the extracted centerline becomes, for example, a straight line.

The image collating unit 104 performs the image collation by using the after-correction image acquired by the image correcting unit 103. The foregoing frequency DP matching method is applied for the palm print and the palm vein similarly to the case of applying for the fingerprint and the finger vein, and a collation result is outputted. In such a manner, the collation result is acquired likewise also when the palm is used as the living body.

Next, the third exemplary embodiment obtained by altering the above-mentioned first embodiment will be explained. Additionally, the changing point from the first exemplary embodiment is a point of using an image acquiring device of a line censor type (see FIG. 11).

Figure 11:
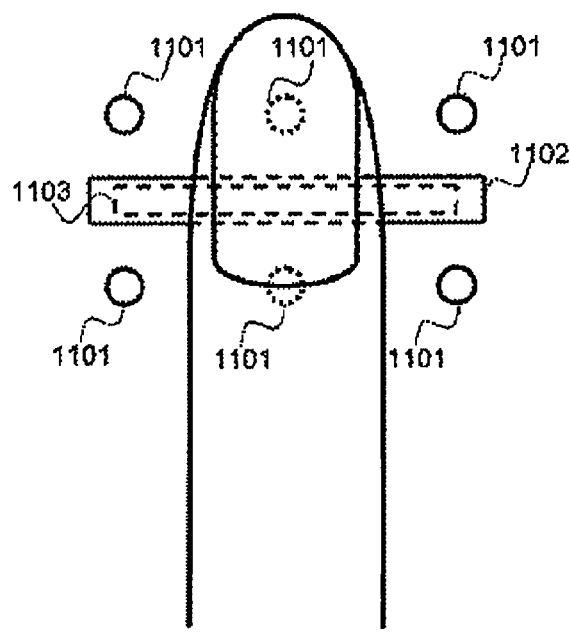
FIG. 11 is a schematic drawing of the image acquiring unit in a third exemplary embodiment of the present invention.

The image acquiring unit (device) in this exemplary embodiment includes near-infrared LEDs 1101, an infrared transparent filter 1102, and an imaging device 1103 (see FIG. 11).

The near-infrared LED 1101 and the infrared transparent filter 1102 are identical to the near-infrared LED 201 and the infrared transparent filter 202 of the foregoing first exemplary embodiment, respectively.

The imaging device 1103 includes a one-dimensional line censor (or a strip-shaped two-dimensional line censor) and a lenticular lens. Assuming such a structure makes it possible to capture the image of one part of the finger in a line shape as the one-dimensional partial image (or the partial image having a rectangular region). And, the captured partial images are jointed together, thereby allowing the image of an entirety of the finger to be synthesized. The image synthesized in such a manner can be used similarly to the case of the image captured by the image acquiring unit in the foregoing first exemplary embodiment.

A reference line extracting unit, an image correcting unit, and an image collating unit of this exemplary embodiment are identical to ones explained in the foregoing first exemplary embodiment. Additionally, the reference line extracting unit and the image correcting unit of the third exemplary embodiment may be configured as follows. This image acquiring unit acquires the one-dimensional or two-dimensional image having a rectangular region to the scanning of the finger because of using the image acquiring device of a line sensor type. Thereupon, the reference line extracting unit of the third exemplary embodiment performs the reference line extraction and the image correction whenever it acquires the image having a rectangular region image by scanning the finger. That is, the reference line extracting unit outputs the after-correction image as follows. At first, the finger is scanned by the image acquiring unit, and the one-dimensional or two-dimensional image with a rectangular region is acquired. The processing of the reference line extracting unit is applied for the acquired image with a rectangular region similarly to the case of the partial image in the lateral direction in the foregoing first embodiment. This allows the centerline to be acquired. And, for example, the image correction of arranging the acquired centerline in the central part of the image is performed so as to yield the pre-decided arrangement. This processing is repeated until the entirety of the finger is scanned. And, by jointing the images corrected for each scan together, the after-correction image is outputted.

As mentioned above, activating the image acquiring unit, the reference line extracting unit, and the image collating unit makes it possible to sequentially performing the image correction after acquiring the image by the scanning of the finger. And, the after-correction image is outputted when the scanning of the finger is finished. This shortens the time ranging from the finishing of the image acquisition to acquisition of the final collation result similarly to the case of the foregoing first exemplary embodiment as compared with the case of performing the image correction after the acquisition of the image. That is, the wait time ranging from the finishing of the manipulation up to acquisition of the collation result is shortened. As a result, quicker response can be gained, and usability is enhanced.

Next, the fourth exemplary embodiment obtained by altering the above-mentioned first embodiment will be explained. Additionally, the changing point from the first exemplary embodiment is a point that a centerline correcting unit is added to the reference line extracting unit.

Figure 12:
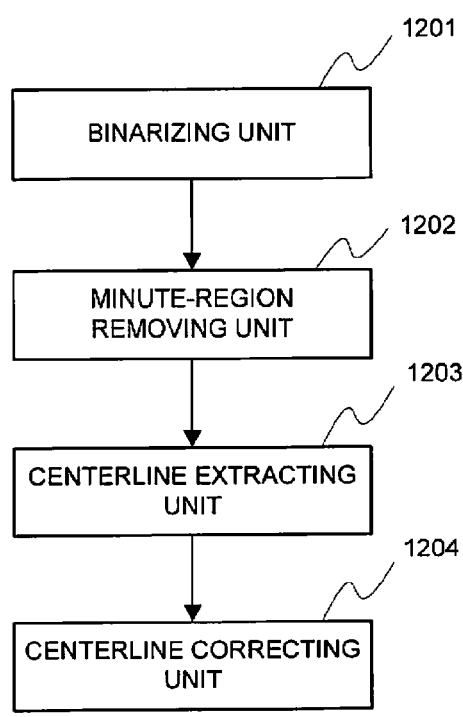
FIG. 12 is a block diagram of the reference line extracting unit in a fourth exemplary embodiment of the present invention.

The reference line extracting unit (device) of the fourth exemplary embodiment is shown in FIG. 12. According to FIG. 12, the reference line extracting unit (device) of the fourth exemplary embodiment includes a binarizing unit 1201, a minute-region removing unit 1202, a centerline extracting unit 1203, and a centerline correcting unit 1204.

The binarizing unit 1201, the minute-region removing unit 1202, and the centerline extracting unit 1203 are similar to that of the foregoing first exemplary embodiment.

The centerline correcting unit 1204 corrects the centerline of the imaging target extracted by the centerline extracting unit 1203 as follows.

The minute-region removing unit 1202 removes the regions other than the region having a maximum area similarly to the case of the foregoing first exemplary embodiment.

Figure 13:
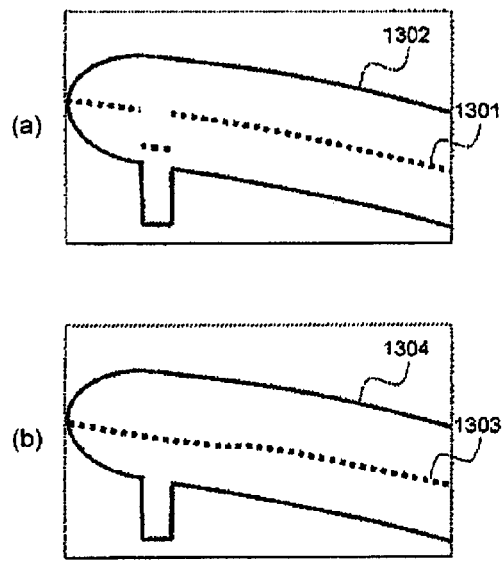
FIG. 13 is an explanatory view of an example of correcting the centerline in the fourth exemplary embodiment of the present invention.

However, the region estimated to be the imaging target and the background, which remains as the region, are contact with each other in the binarized image in some cases (see FIG. 13(*a*)). In such a case, an influence of the background is not eliminated although the minute regions are removed with the area defined as a reference. Thus, the centerline is unnaturally crooked in the portion influenced by the background although the centerline extracting unit extracts the centerline (see FIG. 13(*a*)). Thereupon, the centerline needs to be corrected. For example, the technique of defining the line equivalent to the maximum length as the centerline when two centerlines or more exist is thinkable. Or, the technique of calculating the centerline from a dispersion of the center points is also thinkable.

By the way, originally, the centerline of the finger correctly extracted is an approximately straight line (or a quietly curved line). Thus, for the centerline of the finger obtained by the centerline extracting unit 1203, the centerline correcting unit 1204 performs the processing of changing the coordinate of the center point acquired for a certain partial image to an average value of the coordinates of the center points within a certain scope, which extends ahead of and behind the above center point. For example, the scope for obtaining the averaged value of the coordinates of the center points is defined as a scope equivalent to 10% of the length in the longitudinal direction of the image, and the averaged value of the coordinates is obtained for each above scope. Performing such a change allows the unnaturally crooked portion caused by an influence of the background to be become shaped so as to conform to the tendency of the centerline of the surroundings (see FIG. 13(*b*)). That is, correcting the centerline as mentioned above allows an influence of the background not eliminated by the minute-region removing unit 1202 as well to be alleviated. That is, it becomes possible to extract the more correct centerline of the finger.

Figure 14:
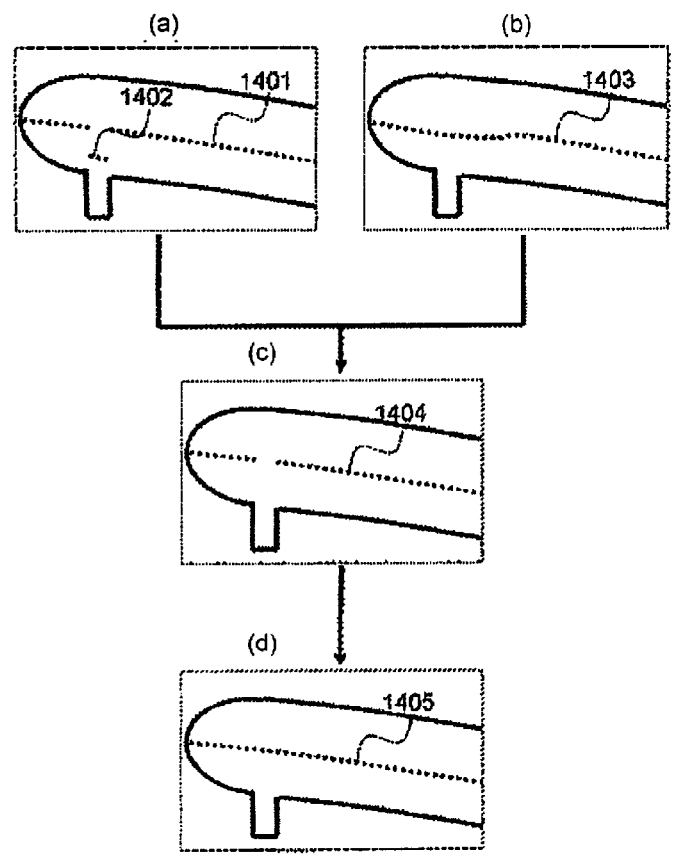
FIG. 14 is an explanatory view of an example of correcting the centerline in the fourth exemplary embodiment of the present invention.

The centerline can be corrected with the method as shown in FIG. 14 in addition to the above-mentioned methods. FIG. 14(*a*) shows the before-correction centerline. FIG. 14(*b*) shows the before-correction averaged value of the coordinates of the center points. In FIG. 14(*c*), the center points exceeding a threshold have been removed. FIG. 14(*d*) shows the after-correction centerline.

That is, for the centerline of the finger acquired by the centerline extracting unit 1203, an averaged value of the coordinates of the center points within a certain scope, which extends ahead of and behind a certain center point, is obtained (see FIG. 14(*b*)). And, the center points exceeding a threshold are removed from the centerline by comparing the centerline of the finger acquired by the centerline extracting unit 1203 with the obtained averaged value of the coordinates (see FIG. 14(*c*)). Thereafter, the coordinate of the removed center point is defined as an average value of the coordinates of the remaining center points, and the after-correction centerline is acquired (see FIG. 14(d)). The coordinates of the center points of the portion unnaturally crooked due to an influence of the background can be removed also with such a method. That is, it becomes possible to alleviate an influence of the background.

And, correcting the centerline as mentioned above makes it possible to acquire more accurate image as compared with the case of the foregoing first exemplary embodiment. And, a precision of the image collation is enhanced.

While the technique of extracting the centerline as the reference line was used in the above-mentioned exemplary embodiments, the technique as well of extracting the contour line instead of the centerline can be adopted likewise.

Also when the contour line is used as the reference line, the partial image having a width of a one-pixel portion is defined as one line similarly to the case of using the centerline. One line of the edge of the image is scanned in the lateral direction (in FIG. 5, the vertical direction), and the coordinates of both edge points of the region of the finger within the line are investigated. The acquired coordinates of both edge points are defined as contour points of the finger in this line. The lines are sequentially updated along the longitudinal direction (in FIG. 5, the horizontal direction), and the contour points of the finger in all of the lines are investigated. In such a manner, the contour points of the region of the finger are extracted. Additionally, the partial image may be defined as the image of plural lines to extract the contour points of the region of the finger for every plural lines similarly to the case of using the centerline.

The image subjected to the movement like the exemplary embodiments mentioned above with at least one part of the contour line acquired as mentioned above defined as the reference line is outputted as the after-correction image.

Figure 15:
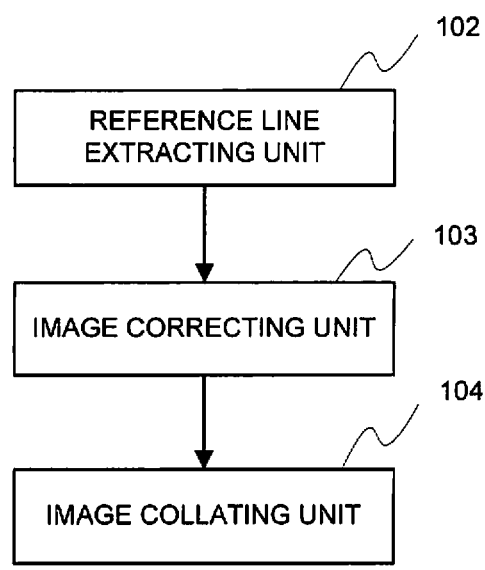
FIG. 15 is a block diagram of the collating device in accordance with the present invention.

FIG. 15 is a block diagram of the collating device in accordance with the present invention.

This collating device includes a reference line extracting unit 102, an image correcting unit 103, and an image collating unit 104. The reference line extracting unit 102 is a device for extracting a predetermined reference line in the image. The image correcting unit 103 is a device for correcting the image by moving (translating) it for each partial image so that the reference line acquired by the reference line extracting unit 102 becomes a pre-determine one. The image collating unit 104 is a device for collating the image corrected by the image correcting unit 103 with a predetermined image (already registered image). This collating device is a device in which the image acquiring unit of the collating unit of FIG. 1 is omitted. Thus, a function/operation of this collating device or the like can be grasped from the above-mentioned explanation, so detailed explanation is omitted.

Figure 16:
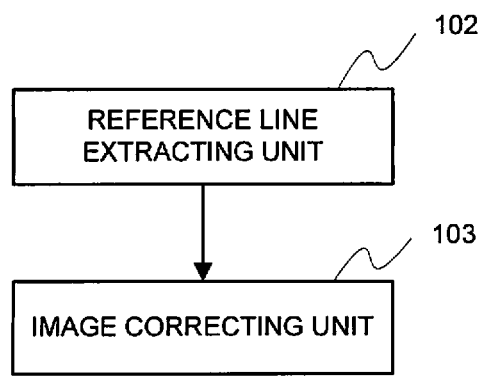
FIG. 16 is a block diagram of the correcting device in accordance with the present invention.

FIG. 16 is a block diagram of the correcting device in accordance with the present invention.

This correcting device includes a reference line extracting unit 102 and an image correcting unit 103. The reference line extracting unit 102 is a device for extracting a predetermined reference line in the image. The image correcting unit 103 is a device for correcting the image by moving (translating) it for each partial image so that the reference line acquired by the reference line extracting unit 102 becomes a pre-determine one. That is, this correcting device is a device in which the image acquiring unit and the image collating device of the collating unit of FIG. 1 are omitted. Thus, a function/operation of this correcting device or the like can be grasped from the above-mentioned explanation, so detailed explanation is omitted.

Figure 17:
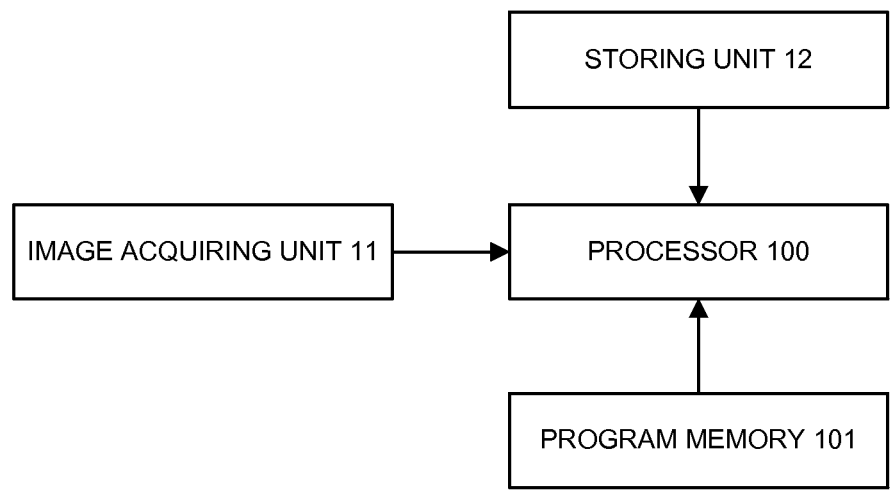
FIG. 17 is a block diagram of an information processing system in accordance with the present invention.
Figure 18:
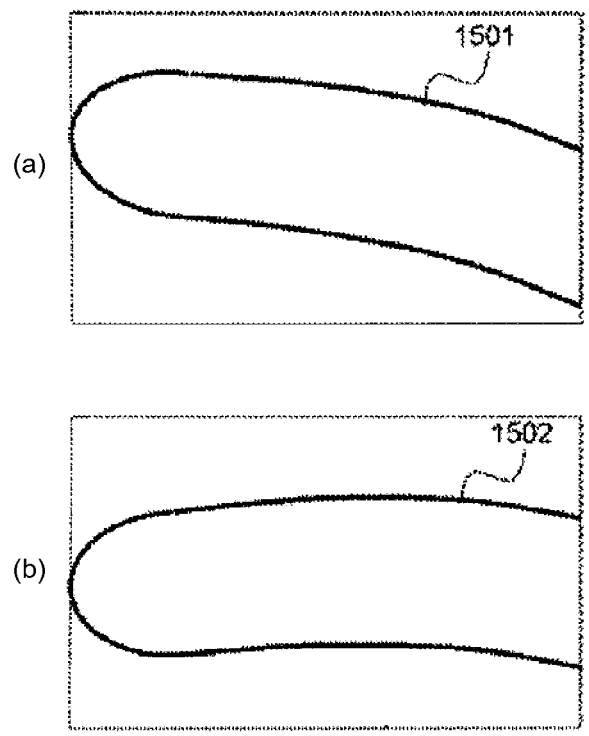
FIG. 18 is an explanatory view of an example of the contour extraction/rotation correction of the prior art.

FIG. 17 is a block diagram of the information processing system having the collating device of the present invention implemented therein.

The information processing system shown in FIG. 17 includes a processor 100, a program memory 101, a storing unit 12, and an image acquiring unit 11.

The program memory 101 has a program filed therein for causing the processor 100 to execute the above-mentioned reference line extracting processing, image correcting processing, and image collating processing. And, the processor 100 operates under this program.

And, the present invention is realized with the above-mentioned computer program.

Additionally, there is no necessity for performing all of the reference line extracting processing, the image correcting processing, and the image collating processing with the program. For example, one part thereof may be configured with hardware.

Above, although the present invention has been particularly described with reference to the preferred embodiments, it should be readily apparent to those of ordinary skill in the art that the present invention is not always limited to the above-mentioned embodiment, and changes and modifications in the form and details may be made without departing from the spirit and scope of the invention.

This application is based upon and claims the benefit of priority from Japanese patent application No. 2008-263483, filed on Oct. 10, 2008, the disclosure of which is incorporated herein in its entirety by reference.

INDUSTRIAL APPLICABILITY

The present invention may be applied to an application of the personal authentication system. The present invention may be applied, for example, to applications such as a log-in system to personal computers and a utilization control system of mobile telephones besides a gate passing control system and an immigration control system. That is, the present invention may be applied for an authentication system at the moment of performing a border control for space and object necessitating security. Further, the present invention may be applied for a system for managing individuals as well, for example, a time/attendance management system.

REFERENCE SIGNS LIST 101 image acquiring unit
102 reference line extracting unit
103 image correcting unit
104 image collating unit
201 near-infrared LED
202 infrared transparent filter
203 imaging device
301 step 301
302 step 302
303 step 303
304 step 304
305 step 305
306 step 306
307 step 307
401 binarizing unit
402 minute-region removing unit
403 centerline extracting unit
501 one line in a lateral direction
502 finger region
503 center point
601 before-correction centerline 602 before-correction finger region
603 after-correction centerline
604 after-correction finger region
701 crooked finger
702 extracted finger region
703 extracted centerline of a finger region
704 after-correction finger region
705 after-correction centerline
801 feature extracting unit
802 linear transforming unit
803 parameter storing unit
804 similarity calculating unit
901 imaging scope guide
902 second finger guide
1001 region of a palm
1002 centerline of a second finger
1003 centerline of a palm
1101 near-infrared LED
1102 infrared transparent filter
1103 imaging device
1201 binarizing unit
1202 minute-region removing unit
1203 centerline extracting unit
1204 centerline correcting unit
1301 before-correction centerline
1302 before-correction finger region
1303 after-correction centerline
1304 after-correction finger region
1401 before-correction centerline
1402 center point influenced by a background
1403 averaged value of coordinates of center points
1404 centerline in which center points exceeding a threshold have been removed
1405 after-correction centerline
1501 after-extraction contour
1502 contour subjected to rotation correction

The invention claimed is:

1. A collating device for collating an image, wherein the image is at least one of the image of a finger and the image of a palm; comprising:
a reference line extracting unit for extracting a predetermined reference line in the image;
an image correcting unit for correcting the image by moving each partial image so that the reference line acquired by said reference line extracting unit becomes a pre-decided one; and
an image collating unit for collating the image corrected by said image correcting unit with a predetermined image,
wherein said image correcting unit is a device for correcting the image by translating in parallel each partial image so that the reference line acquired by said reference line extracting unit becomes a pre-decided one.

2. A collating device according to claim 1, wherein said reference line extracting unit is a device for extracting a centerline or a contour line of the image.

3. A collating device according to claim 1, wherein said reference line extracting unit comprises:
a binarizing unit for extracting one region or plural regions by binarizing the image;
a minute-region removing unit for extracting the region having a maximum area in the region extracted by said binarizing unit; and
a centerline extracting unit for extracting the centerline from the region extracted by said minute-region removing unit.

4. A collating device according to claim 1, wherein said reference line extracting unit comprises:
a binarizing unit for extracting one region or plural regions by binarizing the image;
a minute-region removing unit for extracting the region having a maximum area in the region extracted by said binarizing unit; and
a contour line extracting unit for extracting the contour line from the region extracted by said minute-region removing unit.

5. A collating device according to claim 3, wherein said reference line extracting unit further comprises a centerline correcting unit for correcting the centerline on the basis of the line equivalent to a maximum length when the centerline extracted by said centerline extracting unit is comprised of two lines or more.

6. A collating device according to claim 3, wherein said reference line extracting unit further comprises a centerline correcting unit for, when an averaged value of coordinates of center points within a certain scope, which extends ahead of and behind a certain center point, exceeds a threshold, correcting a centerline by removing the above center point and changing the coordinate of the removed center point to an average value of the coordinates of the remaining center points, said centerline extracted by said centerline extracting unit.

7. A collating device according to claim 4, wherein said reference line extracting unit further comprises a contour line correcting unit for correcting the contour line on the basis of the line equivalent to a maximum length when the contour line extracted by said contour line extracting unit is comprised of two lines or more.

8. A collating device according to claim 4, wherein said reference line extracting unit further comprises a contour line correcting unit for, when an averaged value of coordinates of the contour points within a certain scope, which extends ahead of and behind a certain contour point, exceeds a threshold, correcting a contour line by removing the above contour point and changing the coordinate of the removed contour point to an average value of the coordinates of the remaining contour points, said contour line extracted by said contour line extracting unit.

9. A collating device according to claim 1, wherein said image collating unit comprises:
a device for performing a Fourier transform line by line;
a device for extracting a main component of features by each partial image by performing a linear transform for Fourier amplitude spectra obtained by said Fourier transform; and
a device for computing a similarity with a dynamic programming matching operation by using said main component of features obtained by said linear transform.

10. A collating device according to claim 9 wherein said device for extracting the main component of features by each partial image comprises:
a storing device having basis matrixes stored therein that have been obtained by performing a main component analysis for a learning image set; and
a device for obtaining the main component by performing a linear transform for the image by using said stored basis matrixes.

11. A collating device according to claim 1, further comprising an image acquiring unit for acquiring the image.

12. A collating method of collating an image, wherein the image is at least one of the image of a finger and the image of a palm; comprising:
a reference line extracting step of extracting a predetermined reference line in the image;

an image correcting step of correcting the image by moving it 4-each partial image so that the reference line acquired by said reference line extracting step becomes a pre-decided one; and a collating step of collating the image corrected by said image correcting step with a predetermined image, wherein said image correcting step is a step of correcting the image by translating in parallel each partial image so that the reference line acquired by said reference line extracting step becomes a pre-decided one.

13. A collating method according to claim 12, wherein said reference line extracting step is a step of extracting a centerline or a contour line of the image.

14. A collating method according to claim 12, wherein said reference line extracting step comprises:
   a binarizing step of extracting one region or plural regions by binarizing the image;
   a minute-region removing step of extracting the region having a maximum area from the region extracted by said binarizing step; and
   a centerline extracting step of extracting the centerline from the region extracted by said minute-region removing step.

15. A collating method according to claim 12, wherein said reference line extracting step comprises:
   a binarizing step of extracting one region or plural regions by binarizing the image;
   a minute-region removing step of extracting the region having a maximum area in the region extracted by said binarizing step; and
   a contour line extracting step of extracting the contour line from the region extracted by said minute-region removing step.

16. A collating method according to claim 14, wherein said reference line extracting step further comprises a centerline correcting step of correcting the centerline on the basis of the line equivalent to a maximum length when the centerline extracted by said centerline extracting step is comprised of two lines or more.

17. A collating method according to claim 14, wherein said reference line extracting step further comprises a centerline correcting step of, when an averaged value of coordinates of center points within a certain scope, which extends ahead of and behind a certain center point, exceeds a threshold, correcting a centerline by removing the above center point and changing the coordinate of the removed center point to an average value of the coordinates of the remaining center points, said centerline extracted by said centerline extracting step.

18. A collating method according to claim 15, wherein said reference line extracting step further comprises a contour line correcting step of correcting the contour line on the basis of the line equivalent to a maximum length when the contour line extracted by said contour line extracting step is comprised of two lines or more.

19. A collating method according to claim 15, wherein said reference line extracting step further comprises a contour line correcting step of, when an averaged value of coordinates of the contour points within a certain scope, which extends ahead of and behind a certain contour point, exceeds a threshold, correcting a contour line by removing the above contour point and changing the coordinate of the removed contour point to an average value of the coordinates of the remaining contour points, said contour line extracted by said contour line extracting step.

20. A collating method according to claim 12, wherein said collating step comprises:

a step of for performing a Fourier transform line by line;
a step of for extracting a main component of features by each partial image by performing a linear transform for Fourier amplitude spectra obtained by said Fourier transform; and
a step of computing a similarity with a dynamic programming matching operation by using said main component of features obtained by said linear transform.

21. A collating method according to claim 20, wherein said step of extracting the main component of features by each partial image comprises a step of obtaining the main component by performing a linear transform for the image by using basis matrixes obtained by performing a main component analysis for a learning image set.

22. A non-transitory computer-readable medium encoded with a program for causing a collating device to execute:
   a reference line extracting process of extracting a predetermined reference line in an image;
   an image correcting process of correcting the image by moving each partial image so that the reference line acquired by said reference line extracting process becomes a pre-decided one; and
   a collating process of collating the image corrected by said image correcting process with a predetermined image,
   wherein said image correcting process is a process of correcting the image by translating in parallel each partial image so that the reference line acquired by said reference line extracting process becomes a pre-decided one;
   wherein the image is at least one of the image of a finger and the image of a palm.

23. A non-transitory computer-readable medium encoded with a program according to claim 22, wherein said reference line extracting process is a process of extracting a centerline or a contour line of the image.

24. A non-transitory computer-readable medium encoded with a program according to claim 22, wherein said reference line extracting process comprises:
   a binarizing process of extracting one region or plural regions by binarizing the image;
   a minute-region removing process of extracting the region having a maximum area in the region extracted by said binarizing process; and
   a centerline extracting process of extracting the centerline from the region extracted by said minute-region removing process.

25. A non-transitory computer-readable medium encoded with a program according to claim 22, wherein said reference line extracting process comprises:
   a binarizing process of extracting one region or plural regions by binarizing the image;
   a minute-region removing process of extracting the region having a maximum area in the region extracted by said binarizing process; and
   a contour line extracting process of extracting the contour line from the region extracted by said minute-region removing process.

26. A non-transitory computer-readable medium encoded with a program according to claim 24, wherein said reference line extracting process comprises a centerline correcting process of correcting the centerline on the basis of the line equivalent to a maximum length when the centerline extracted by said centerline extracting process is comprised of two lines or more.

27. A non-transitory computer-readable medium encoded with a program according to claim 24, wherein said reference line extracting process comprises a centerline correcting process of, when an averaged value of coordinates of center points within a certain scope, which extends ahead of and behind a certain center point, exceeds a threshold, correcting a centerline by removing the above center point and changing the coordinate of the removed center point to an average value of the coordinates of the remaining center points, said centerline extracted by said centerline extracting process.

28. A non-transitory computer-readable medium encoded with a program according to claim 25, wherein said reference line extracting process comprises a contour line correcting process of correcting a contour line by changing the coordinate of a contour point to an average value of the coordinates of the contour points within a certain scope, which extends ahead of and behind the above contour point, said contour line extracted by said contour line extracting process.

29. A non-transitory computer-readable medium encoded with a program according to claim 25, wherein said reference line extracting process comprises a contour line correcting process of, when an averaged value of coordinates of contour points within a certain scope, which extends ahead of and behind a certain contour point, exceeds a threshold, correcting a contour line by removing the above contour point and changing the coordinate of the removed contour point to an average value of the coordinates of the remaining contour points, said contour line extracted by said contour line extracting process.

30. A non-transitory computer-readable medium encoded with a program according to claim 22, wherein said collating process comprises:
   a process of for performing a Fourier transform line by line;
   a process of extracting a main component of features by each partial image by performing a linear transform for Fourier amplitude spectra obtained by said Fourier transform; and
   a process of computing a similarity with a dynamic programming matching operation by using said main component of features obtained by said linear transform.

31. A non-transitory computer-readable medium encoded with a program according to claim 30, wherein said process of extracting the main component of features by each partial image comprises a process of obtaining the main component by performing a linear transform for the image by using basis matrixes obtained by performing a main component analysis for a learning image set.

* * * * *